(12) United States Patent
Murui

(10) Patent No.: US 6,444,839 B1
(45) Date of Patent: Sep. 3, 2002

(54) METHOD OF PRODUCING ROSEMARINIC ACID

(75) Inventor: Takeo Murui, Tokyo (JP)

(73) Assignee: Salad Cosmo Co., Ltd., Gifu (JP)

( * ) Notice: Subject to any disclaimer, the term of this patent is extended or adjusted under 35 U.S.C. 154(b) by 30 days.

(21) Appl. No.: 09/605,150

(22) Filed: Jun. 28, 2000

(51) Int. Cl.$^7$ .............................. C07C 69/76; C12P 7/62
(52) U.S. Cl. ........................ 560/75; 435/135; 424/195.1
(58) Field of Search ............................ 560/75; 562/75; 424/195.1; 435/135

(56) References Cited

U.S. PATENT DOCUMENTS

| 4,354,035 A | 10/1982 | Christ et al. ................... 560/75 |
| 5,869,340 A | * 2/1999 | Shetty |

OTHER PUBLICATIONS

Derwent abstract (Acc. No. 1999–495764) of EP 941672. Jodlbauer et al. (1999). Foodstuff containing essential fatty acid supplement for prophylaxis of degenerative vascular disease or strengthening and stabilizing cardiovascular system.*
Derwent abstract (Acc. No. 1999–040629) of JP 10298098. Hiroyo et al. (1998). Lipoxygenase inhibitor used in anti-inflammatory agent—contains luteolin or chrysoeriol.*
Derwent abstract (Acc. No. 2000–368836) of JP 200086510. Chihiro et al. (2000). Histamine free inhibitor useful for prevention and treatment of allergic disorder.*
Yamamoto et al. (1998). Inhibitors of arachidonate lipoxygenase from defatted perilla seed. Journal of Agricultural and Food Chemistry 46(3): 862–865.*
Patent Abstracts of Japan, 07–187989, Jul. 25, 1995.
Patent Abstracts of Japan, 10–101572, Apr. 21, 1998.
Patent Abstract, 59–132894, Jul. 31, 1984.
Patent Abstract, 62–032889, Feb. 12, 1987 (Japanese Examined Patent Publication No. 1–29558).

* cited by examiner

*Primary Examiner*—Ralph Gitomer
*Assistant Examiner*—Mahreen Chaudhry
(74) *Attorney, Agent, or Firm*—Foley & Lardner

(57) ABSTRACT

Rosemarinic acid or its concentrate is made from seeds of lamiaceous plants in a predetermined period of germination. The method makes it possible to make the rosemarinic acid in any period through the year. High productivity can be achieved by small production facility since high-density cultivation of germinated seed is possible and a cultivation period is short. An amount of rosemarinic acid is rapidly increased after start of germination, and an increasing amount usually becomes maximum five to eight days after start of cultivation. Power obtained by pulverizing dry germinated seeds contains 3 to 5% of rosemarinic acid and can be used for various purposes. An extract obtained by water soluble alcohol from the powder and a fraction obtained by fractioning the extract by an organic solvent are concentrated containing about 15% and 30% of rosemarinic acid respectively. When each concentrate is processed by column chromatography, isolated 99%-rosemarinic acid is obtained.

9 Claims, No Drawings

METHOD OF PRODUCING ROSEMARINIC ACID

BACKGROUND OF THE INVENTION

1. Field of the Invention

This invention relates to a method of producing rosemarinic acid or concentrate containing a high concentration of rosemarinic acid from germinated seeds of lamiaceous plants.

2. Description of the Prior Art

Rosemarinic acid is expected to be widely used as water-soluble strong antioxidant in the field of foods, as cosmetics and ultraviolet absorbent in the filed of cosmetics, and for pharmaceutical activity such as anti-inflammatory effect, antithrombotic effect and antiproliferative activity. It is known that lamiaceous, umbellifarous, and boroginaceous plants contain rosemarinic acid. Particularly lamiaceous plants contain a large amount of rosemarinic acid. Rosemarinic acid is mainly present as glucoside in leaves of lamiaceous plants although seeds thereof contain a small amount of rosemarinic acid.

With respect to the industrial production of rosemarinic acid, Japanese Unexamined Patent Publication-Nos. 7-187989A (1995) and 10-101572A (1998) disclose methods of extracting rosemarinic acid from a plant body such as leaves of perilla respectively. Furthermore, Japanese Unexamined Patent Publication No. 59-132894A (1984) and Japanese Examined Patent Publication No. 1-29558B (1989) disclose methods of cultivating tissue cells of lamiaceous plants respectively. However, since leaves of perilla can be obtained only in a specific season, rosemarinic acid cannot be produced throughout the year. Furthermore, the industrial production of rosemarinic acid requires a vast cultivation land and a cold storage so that perilla leaves are prevented from deterioration and decomposition for a long period. Thus, the industrial production of rosemarinic acid has a number of limitations. Additionally, it is difficult to control cultivation conditions in the tissue cultivation method, and the composition of product is unstable. Thus, basic problems remain unsolved in the industrial production of rosemarinic acid. A stable and efficient method of producing rosemarinic acid has not been established yet though usability of rosemarinic acid is well known.

SUMMARY OF THE INVENTION

Therefore, an object of the present invention is to provide a method of economically and efficiently producing rosemarinic acid or a concentrate containing a high concentration of rosemarinic acid.

To solve the aforesaid problems, the inventor examined variations of rosemarinic acid content in the seeds of lamiaceous plants during germination. The inventor found that an amount of rosemarinic acid contained in the seed of lamiaceous plants was obviously increased in a specific period of the germination although the seed originally contained only a small amount of rosemarinic acid. The present invention was made on the basis of this finding.

More specifically, an amount of rosemarinic acid contained in the seed does not shown a clear change in a period when the seed absorbs water and does not change its appearance. However, the amount of rosemarinic acid is rapidly increased at a stage where germination is observed and then it is gradually decreased after having reached its maximum. This property is common to seeds of lamiaceaous plants and is not lost after the seeds have been stored for a long period. Accordingly, it is possible to produce rosemarinic acid with a higher yield by using the germinated seed than by using non-germinated seed as starting material.

Furthermore, since the present invention is practiced inside a room, cultivation can be done in an industrial scale throughout the year even in a land unsuitable for raising the lamiaceous plants outdoors. Furthermore, since the seeds are germinated in a growing basket, a higher density of cultivation can be realized as compared with raising lamiaceous plants outdoors. Additionally, since a growth period is short, cultivation can be repeated at a number of times. Consequently, high productivity can be achieved even when growing or extracting facilities are small in scale and accordingly, the method of the invention can achieve larger economical improvement than the conventional raising outdoors.

Preferably, the lamiaceous plants are one or more plants belonging to subfamilies of *Stachyoideae, Lavanduloideae, Ocimoideae*, or *Ajugoideae*. Concrete examples include *perilla frutescens* BRITT. var. *japonica* HARA, *perilla frutescens* BRITT. var. *acuta* KUDO, and *perilla frutescens* BRITT. var. *acuta* KUDO *forma vidis* MAKINO. The seeds of lamiaceous plants germinate for 3 to 20 days or more preferably, for 5 to 8 days. Germinated seed is suitably dried and hull is removed from them. The germinated seed is fine ground into powder by a grinder. The powder can be used for various purposes as a composition containing rosemarinic acid. Further, an alcoholic extract from the powder can be served as a concentrate of rosemarinic acid. When the alcoholic extract is fractionated by water and water-insoluble organic solvent, a concentrate with a higher concentration can be obtained. Additionally, substantially pure rosemarinic acid can be obtained by column chromatography etc.

Other objects, features and advantages of the present invention will become clear upon reviewing the following description of the preferred embodiment.

DETAILED DESCRIPTION OF THE PREFERRED EMBODIMENT

One embodiment of the present invention will now be described. Lamiaceous plants referred to herein belong to Labiatae in the plant taxonomy. More preferably, the lamiaceous plants are one or more plants belonging to *Stachyoideas, Lavanduloideae, Ocimoideae,* or *Ajugoideae*. As a suitable example, the lamiaceous plants may be one or more of *perilla frutescens* BRITT. var. *japonica* HARA, *perilla frutescens* BRITT. var. *acuta* KUDO, *perilla frutescens* BRITT. var. *acuta* KUDO *forma vidis* MAKINO, *perilla frutescens* BRITT. var. *crispa* DEANE, *mentha piperita* HUDS, *thymus vulgaris* L., *Salvia officinalis* L. all of which belong to *Stachyoideae. lavandula angus tifolia* MILL belonging to *Lavanduloideae, ocimum basilicum* L. belonging to *Ocimoideae*, and *rosmarinus officianlis* L. belonging to *Ajugoideae*. Of them, *perilla frutescens, perilla frutescens* BRITT. var. *acuta* KUDO, *perilla frutescens* BRITT. var. *acuta* KUDO *forma vidis* MAKINO and *perilla frutescens* BRITT. var. *crispa* DEANE, all of which are classified into *Stachyoideae*, are particularly suitable for starting material since an increased amount of rosemarinic acid is large in each of them.

The following describes a method of obtaining germinated seeds of the above-mentioned lamiaceous plants. Vessels, instruments and equipment used to germinate the seeds are not limited particularly. A rotary germination drum (not shown) used to cultivate alfalfa sprout etc. is usually advantageous in the germination of seeds. Seeds of one laminaceous plant are immersed in water whose temperature is at or below 30° C. Immersion is continued for 3 to 12 hours. The seeds having absorbed water are put into a dish-shaped cultivation basket. The seeds are left in the basket at 25° C. to 30° C. for about 15 hours. The seeds are suitably sprinkled with water in the interim so as to be prevented from being dried. The seeds are then transferred into the germination drum. The seeds are kept in the germination drum for 3 to 20 days or more preferably, for 5 to 8 days while being subjected to light. The seeds may be cultivated in a dark place although an amount of rosemarinic acid contained in the seeds is reduced as compared with the case where the seeds are subjected to light. The germination drum is adapted to be turned five turns per day. With turn of the germination drum, the seeds are located upside down, namely, upper seeds are located lower, whereas lower seeds are located upward, whereupon oxygen and light are uniformly supplied to the seeds. An atmospheric temperature ranges between 25° C. and 30° C. during germination. Furthermore, water is sprinkled in the interval of 3 to 5 hours.

An amount of rosemarinic acid contained in the seed does not change for two or three days after start of germination. Subsequently, the amount of rosemarinic acid is rapidly increased up to a maximum and is thereafter decreased gradually. The number of days required for the amount of rosemarinic acid to reach its maximum cannot uniformly be defined since it is affected by the cultivation conditions including temperature, amount of light, and amount of oxygen supplied. However, under the above-mentioned conditions, 5 to 8 days are generally required after start of germination for an amount of rosemarinic acid to reach its maximum. Upon reach of the maximum amount, germinated seed is 2 to 4 cm long, and this state of the germinated seed corresponds to a germination stage when two leaves are appeared. Furthermore, a time period for which the maximum amount of rosemarinic acid contained in the seed is maintained is short, namely, is usually one or two days, and strictly speaking, it is within one day. Additionally, a maximum amount of rosemarinic acid depends upon an amount of light and an amount of oxygen supplied to the seed during germination and particularly, upon the amounts of light and oxygen supplied to the seed after the germinated seed has grown to the length of 0.5 cm or more. The maximum amount of rosemarinic acid is usually about six times as large as that before germination. An amount of rosemarinic acid is increased even when the seed is subjected to no light. However, it is efficient to irradiate light of 100 Lux onto the seed continuously from the third day or fourth day after start of germination.

An amount of seeds to be put into the germination drum is particularly important. When the amount of seeds is excessively large, the seeds are not efficiently agitated due to an increase in the volume with germination. As a result, a sufficient amount of oxygen cannot be supplied to the seeds and a time period for which the seeds are subjected to light is reduced. Accordingly, a sufficient increase of rosemarinic acid cannot be expected. An amount of seeds to be put into the germination drum once is up to 20% the volumetric capacity of the germination drum. An ideal amount of seeds is 8% the volumetric capacity of the drum or less. Furthermore, an amount of sprinkled water is about 20 litters for every 1 kg of seed. TABLE 1 shows variation of rosemarinic acid content in the germinated seed corresponding to 1 kg of seeds of *perilla frutescens* BRITT, var *japonica* HARA cultivated under the above-described conditions.

TABLE 1

| Number of days | Content of rosemarinic Acid in gram (per germinated seed corresponding to 1 kg of seeds) | Light in Lux |
| --- | --- | --- |
| 0 | 4.0 | |
| 1 | 4.5 | None |
| 2 | 5.1 | None |
| 3 | 9.2 | 200 |
| 4 | 16.1 | 200 |
| 5 | 20.0 | 200 |
| 6 | 19.2 | 200 |
| 6 | 17.2 | None |
| 7 | 24.7 | 200 |
| 7 | 17.9 | None |
| 8 | 22.3 | 200 |
| 8 | 18.2 | None |
| 9 | 22.0 | 200 |
| 10 | 22.2 | 200 |
| 12 | 20.8 | 200 |
| 13 | 18.2 | 200 |
| 14 | 15.3 | 200 |
| 15 | 10.5 | 200 |
| 16 | 8.6 | 200 |

Each seed contains rosemarinic acid before it is germinated. However, the content of rosemarinic acid is only about 4 g per 1 kg of seeds. As obvious from TABLE 1, the amount of rosemarinic acid rapidly increases from the third day of the germination and reaches its maximum at the seventh day of the germination. At that time, the content of rosemarinic acid is about 25 g per 1 kg of seeds, which is six times as large as that before germination. Accordingly, it is possible to produce rosemarinic acid with high yield by using germinated seed at this stage as starting material.

The rotary germination drum is used for preparing germinated seed in the embodiment. In an alternative, the seed having absorbed water is put into a dish-shaped basket or a 2 mm mesh basket and is agitated while being put into another basket of the same type. In this case, substantially the same effect can be achieved when the seeds are germinated under the same conditions including the temperature, an amount of water to be sprinkled, an amount of light, etc. as in use of the germination drum.

The following describes steps of the method of extracting rosemarinic acid and a concentrate thereof from the seeds of *perilla frutescens* BRITT. var. *japonica* HARA.

Milling of germinated seed

Germinated seed of *perilla frutescens* BRITT. var. *japonica* HARA contains about 95% of water by weight at the seventh day of cultivation. Accordingly, freeze-drying, drying by heating with hot air, or solar-drying is carried out for the germinated seed so that a dry germinated seed containing 2% of water by weight or less is obtained. Hull is removed from the dried germinated seed using a 5 mm mesh screen. Thereafter, the dried germinated seed is fine ground by a grinder. The resultant powder contains about 4.5% of rosemarinic acid by weight. Accordingly, the powder can be utilized as a composition containing rosemarinic acid.

Methanol extraction

The powder of germinated seed is immersed in a non-polar organic solvent such as hexane or in a weak polar organic solvent such as diethyl ether so that oil component is separated. A solvent layer is then eliminated by filtration. The residual solvent is removed from extraction residue under reduced pressure so that defatted material is obtained. This step may be omitted with respect to the germinated seed cultivated for 14 or more days. The defatted material is immersed in methanol having a weight 3 to 20 times larger than the defatted material or methanol containing a small amount of water while being heated. Insoluble residue is filtered to be removed so that extracted liquid is obtained. When the methanol containing no water is used, an amount of saccharides to be extracted is decreased, so that a concentrate containing a higher content of rosemarinic acid is obtained. A high extracting efficiency necessitates a long period of extraction. The extracting solvent includes lower monovalent alcohols such as ethanol or isopropyl alcohol, and water-soluble alcohol as well as methanol. The temperature of the alcohol may be equal to the room temperature. Preferably, a reflux condenser can efficiently be used so that extraction takes place when the temperature of alcohol is approximated to a boiling temperature thereof.

Pressure may be atmospheric during the extraction. An extracting time period depends upon the temperature and ranges between 1 and 15 hours. The yield can be improved when insoluble residue is repeatedly extracted. The concentrate (or methanol extract) containing about 15% of rosemarinic acid by weight was obtained when extracting solvent was removed by a vacuum concentrator.

Ethyl acetate fractionation

The aforesaid methanol extract is dissolved in water whose weight is about ten times larger than that thereof. Ethyl acetate whose amount is substantially equal to that of the water is further added. A container containing the mixture is vigorously shaken and thereafter left stationary. The ethyl acetate layer is transferred to another container, and the solvent is removed by a vacuum concentrator, whereupon a high concentrate containing 30% of rosemarinic acid by weight (ethyl acetate fraction) is obtained.

Column fractionation

The ethyl acetate fraction is dissolved in water whose amount is about five times as large as the weight of the fraction. Thereafter, insoluble matter is removed by a centrifugal separator. Supernatant liquid is put into a column filled with silica gel chemically bonded with octadecylsilyl groups. After 15% -methanol (methanol:water=15:85 by volume) is caused to flow through the column, the fraction eluted by 30%-methanol (methanol:water=30:70 by volume) is collected. The solvent is removed from the fraction by a vacuum concentrator, whereupon 99% of isolated rosemarinic acid by weight is obtained.

EXAMPLE 1

Seeds of *perilla frutescens* BRITT. var. *japonica* HARA, which weighed 7 kg, were immersed for 8 hours in water whose temperature was at 22° C. The weight of the seeds corresponded to about 8% of space of the germination drum in which the seeds were put. Thereafter, the water was removed and the seeds were left in a dark place for 15 hours. A small amount of water was sprinkled in the interval of 5 hours in that period. The seeds were then transferred into the germination drum in which the temperature was maintained at 28° C. The germination drum was turned five turns per day, and water of 140 liters was sprinkled in the interval of 4 hours. The germination drum was subjected to light of about 200 Lux from the third day of the cultivation and on.

The cultivation was completed at the seventh day. Germinated seeds weighing 68.5 kg were obtained. The germinated seeds were frozen at −20° C. and thereafter dried by a freeze-drier until the water content was reduced to 2%, whereupon dried germinated seeds weighing 5.62 kg were obtained. The obtained germinated seeds were passed through a 5 mm mesh screen so that hull was removed from the dried matter. The germinated seeds were then fine-ground by a grinder such that ground powder of 3.52 kg containing 4.8% of rosemarinic acid by weight was obtained. The content of rosemarinic acid was analyzed by high performance liquid chromatography.

EXAMPLE 2

The ground powder of 1 kg obtained in Example 1 was immersed in 5 liters of hexane. A condenser was provided so that the hexane was refluxed at 60° C. for 5 hours for defatting. The hexane was removed after cooling, and insoluble matter was heated under the reduced pressure so that residual hexane was removed, whereupon defatted matter was obtained. The defatted matter was immersed in 5 liters of methanol and heated at 60° C. for 5 hours with agitation. The defatted matter was then filtered so that insoluble matter was removed. The solvent was removed from methanol extract liquid by a vacuum concentrator, whereupon methanol extract weighing 265.2 g was obtained. The obtained methanol extract was a concentrate containing 18.1% of rosemarinic acid by weight.

EXAMPLE 3

The methanol extract obtained at Example 2 was dissolved in one liter of water. One liter of ethyl acetate was added and the mixture was vigorously shaken. The mixture was then left stationary for a while. The upper layer was transferred to another vessel and the solvent was removed under the reduced pressure, whereupon a high concentrate weighing 132.5 g and containing 35.3% of rosemarinic acid by weight was obtained.

EXAMPLE 4

The concentrate of 10 g obtained in Example 3 was dispersed in 300 milliliter of water. Insoluble matter was removed by a high speed centrifugal separator which was driven at 15000 rpm for 30 minutes. All supernatant liquid was put into a column filled with about 1 kg of silica gel coupled with octadecylsilyl groups. After 4 liter of 15%-methanol (methanol:water=15:85 by volume) was caused to flow through the column, the fraction eluted by 5.5 liter of 30%-methanol (methanol:water=30:70 by volume) was collected. The solvent was removed from the collected fraction by a vacuum concentrator, whereupon 2.33 g of 99.1% of isolated rosemarinic acid by weight was obtained.

EXAMPLE 5

Seeds of *perilla frutescens* BRITT. var. *japonica* HARA, which weighed 7 kg, were grown for 7 days under the same conditions as in Example 1. However, the seeds were not subjected to light during the growth. Germinated seed weighing 65.3 kg were obtained. The germinated seed was dried with sun light to get dry germinated seed. Subsequently, the same operation as that in the Example 1 was performed such that ground powder of 3.63 kg containing 3.4% of rosemarinic acid by weight was obtained.

EXAMPLE 6

Seeds of *perilla frutescens* BRITT. var. *japonica* HARA, which weighed 7 kg, were grown for 7 days under the same conditions as in Example 1. However, the irradiation of light to which the seeds were subjected was at 500 Lux. Germinated seeds weighing 68.0 kg were obtained. Hot air drying process was carried out for the germinated seeds at 60° for 6 hours. Subsequently, the same operation as that in the Example 1 was performed such that ground powder of 3.71 kg containing 5.0% of rosemarinic acid by weight was obtained.

EXAMPLE 7

Seeds of *perilla frutescens* BRITT. var. *japonica* HARA, which weighed 7 kg, were grown for 10 days under the same conditions as in Example 1. Germinated seeds weighing 69.1 kg were obtained. The germinated seeds were frozen at −20° C. and thereafter dried by a freeze dryer into dried matter. Subsequently, the same operation as that in the Example 1 was performed such that ground powder of 3.55 kg containing 4.1% of rosemarinic acid by weight was obtained.

EXAMPLE 8

The ground powder obtained in Example 7 was processed in Examples 2 to 4 such that the concentrate weighing 1.85 g and containing 98.5% of rosemarinic acid was obtained.

EXAMPLE 9

Seeds of lavender, which weighed 1 kg, were immersed in water at 26° C. for 12 hours. Thereafter, the water was removed and the seeds were left in a dark place for 10 hours. A small amount of water was sprinkled in the interval of 3 hours in that period. The seeds were then transferred into a plastic basket in which the temperature was maintained at 26° C. The seeds were transferred into another basket of the same type once every day and sufficiently mixed simultaneously. The seeds were subjected to light of about 200 Lux from the third day of the cultivation and on. The cultivation was completed at the fifth day. Germinated seeds weighing 8.32 kg were obtained. The germinated seeds were dried in the sun such that dried matter weighing 0.88 kg was obtained. The dried matter was passed through a 3 mm mesh screen so that hull was removed therefrom. The dried matter was then ground by a grinder such that ground powder of 0.45 kg containing 3.5% of rosemarinic acid by weight was obtained.

EXAMPLE 10

Seeds of peppermint, which weighed 1 kg, were grown for eight days under the same conditions as in Example 8, so that germinated seeds weighing 7.58 kg were obtained. The germinated seeds were dried in the sun such that dried matter of 0.82 kg was obtained. Subsequently, the same operation as that in the Example 1 was performed such that ground powder of 0.39 kg containing 3.8% of rosemarinic acid by weight was obtained.

The foregoing description of the preferred embodiment was merely illustrative of the principles of the present invention and not to be construed in a limiting sense. Various changes and modifications will become apparent to those of ordinary skill in the art. All such changes and modifications are seen to fall within the scope of the invention as defined by the appended claims.

What is claimed is:

1. A method of producing rosemarinic acid or its concentrate, comprising:

germinating, while agitating, at least one seed of a lamiaceous plant until a content of rosemarinic acid in said seed or seeds increases more than 4 fold, as compared to the content of rosemarinic acid in said seed or seeds prior to said germinating, in order to produce rosemarinic acid or a concentrate containing rosemarinic acid and wherein, after said germinating, said seed or seeds comprise a raw material.

2. A method according to claim 1, wherein said rosemarinic acid is extracted from the germinated seeds of the lamiaceous plants using a hydrophilic organic solvent.

3. A method according to claim 1, wherein said lamiaceous plants include one or more kinds of plants belonging to subfamilies of *Stachyoideae*, *Lavanduloideae*, *Ocimoideae*, and *Ajugoideae*.

4. A method according to claim 3, wherein said subfamily of *Stachyoideae* includes *perilla frutescens* BRITT. var. *japonica* HARA *perilla frutescens* BRITT. var. *acuta* KUDO, *perilla frutescens* BRITT. var. *acuta* KUDO *forma vidis* MAKINO, and/or *perilla frutescens* BRITT. var. *crispa* DEANE.

5. A method of producing rosemarinic acid or its concentrate according to claim 1, wherein the germinated seed or seeds of said lamiaceous plants comprise the seed or seeds from the 4th day to the 13th day after the initiation of germination.

6. A method according to claim 2, wherein said hydrophilic organic solvents comprise lower monovalent alcohols.

7. A method of producing rosemarinic acid or its concentrate according to claim 1; further comprising, during said germinating, after the 3rd day of the 4th day, irradiating seed or seeds with light of more than 100 Lux.

8. A method of producing rosemarinic acid or its concentrate according to claim 1, further comprising:

providing a rotating germination device; and agitating said seed or seeds in said rotating germination device during said germinating.

9. A method of producing rosemarinic acid or its concentrate according to claim 2, wherein, when rosemarinic acid is extracted from said germinated seed or seeds using a hydrophilic organic solvent, said acid is extracted near the boiling point of the relevant organic solvent.

* * * * *

UNITED STATES PATENT AND TRADEMARK OFFICE
CERTIFICATE OF CORRECTION

PATENT NO. : 6,444,839 B1
DATED : September 3, 2002
INVENTOR(S) : Tateo Murui

It is certified that error appears in the above-identified patent and that said Letters Patent is hereby corrected as shown below:

<u>Title page,</u>
Item [75], Inventor, please delete "Takeo Murui" and insert -- Tateo Murui --.

<u>Column 8,</u>
Line 55,

Please add the following claims:

--10. A method of producing a rosemarinic acid-containing product comprising:

germinating at least one seed of a lamiaceous plant under conditions and for a period of time sufficient to produce a substantial increase in the content of rosemarinic acid in said seed or seeds as compared to the content of rosemarinic acid in said seed or seeds prior to said germinating;

discontinuing the germinating; and recovering from the germinated seeds a rosemarinic acid-containing product having a yield of rosemarinic acid per seed that is higher than a corresponding product produced from said seeds prior to germination, wherein said recovering further comprises:

removing a hull or hulls from said seed or seeds;

drying said seed or seeds; and grinding said seed or seeds to obtain a powder; and wherein a rosemarinic acid content of said powder is 3.4 to 5.0 percent by weight.

11. A method of producing a rosemarinic acid-containing product comprising:

germinating at least one seed of a lamiaceous plant under conditions and for a period of time sufficient to produce a substantial increase in the content of rosemarinic acid in said seed or seeds as compared to the content of rosemarinic acid in said seed or seeds prior to said germinating;

discontinuing the germinating; and recovering from the germinated seeds a rosemarinic acid-containing product having a yield of rosemarinic acid per seed that is higher than a corresponding product produced from said seeds prior to germination, wherein said recovering further comprises:

removing a hull or hulls from said seed or seeds;

drying said seed or seeds; and grinding said seed or seeds to obtain a powder;

UNITED STATES PATENT AND TRADEMARK OFFICE
CERTIFICATE OF CORRECTION

PATENT NO.    : 6,444,839 B1
DATED         : September 3, 2002
INVENTOR(S)   : Tateo Murui It is certified that error appears in the above-identified patent and that said Letters Patent is hereby corrected as shown below:

after said grinding, immersing said powder in a solvent to separate an oil component from said powder;

separating insoluble residue from said solvent to obtain defatted residue;

immersing said defatted residue in a second solvent;

extracting said rosemarinic acid from said defatted residue; and separating a solution comprising said second solvent and rosemarinic acid from said defatted residue, and wherein a rosemarinic acid content of said solution is from about 15 to 18.1 percent by weight.

12. A method of producing a rosemarinic acid-containing product comprising:

germinating at least one seed of a lamiaceous plant under conditions and for a period of time sufficient to produce a substantial increase in the content of rosemarinic acid in said seed or seeds as compared to the content of rosemarinic acid in said seed or seeds prior to said germinating;

discontinuing the germinating; and recovering from the germinated seeds a rosemarinic acid-containing product having a yield of rosemarinic acid per seed that is higher than a corresponding product produced from said seeds prior to germination, wherein said recovering further comprises:

removing a hull or hulls from said seed or seeds;

drying said seed or seeds; and grinding said seed or seeds to obtain a powder;

UNITED STATES PATENT AND TRADEMARK OFFICE
CERTIFICATE OF CORRECTION

PATENT NO. : 6,444,839 B1
DATED : September 3, 2002
INVENTOR(S) : Tateo Murui

It is certified that error appears in the above-identified patent and that said Letters Patent is hereby corrected as shown below:

after said grinding, immersing said powder in a solvent to separate an oil component from said powder;

separating insoluble residue from said solvent to obtain defatted residue;

immersing said defatted residue in a second solvent;

extracting said rosemarinic acid from said defatted residue, to form a first solution; and separating the first solution comprising said second solvent and rosemarinic acid from said defatted residue, wherein said extracting further comprises:

heating said defatted residue immersed in said second solvent in a reflux condenser;

wherein said separating step further comprises:

dissolving said first solution in water;

adding ethyl acetate to said first solution dissolved in water to form a mixture; and separating a second solution comprising ethyl acetate and said rosemarinic acid from said mixture; and wherein a rosemarinic acid content of said second solution is from 30 to 35.3 percent by weight.

13. A method of producing a rosemarinic acid-containing product comprising:

germinating at least one seed of a lamiaceous plant under conditions and for a period of time sufficient to produce a substantial increase in the content of rosemarinic

UNITED STATES PATENT AND TRADEMARK OFFICE
CERTIFICATE OF CORRECTION

PATENT NO. : 6,444,839 B1
DATED : September 3, 2002
INVENTOR(S) : Tateo Murui

It is certified that error appears in the above-identified patent and that said Letters Patent is hereby corrected as shown below:

acid in said seed or seeds as compared to the content of rosemarinic acid in said seed or seeds prior to said germinating;

discontinuing the germinating; and recovering from the germinated seeds a rosemarinic acid-containing product having a yield of rosemarinic acid per seed that is higher than a corresponding product produced from said seeds prior to germination, wherein said recovering further comprises:

removing a hull or hulls from said seed or seeds;

drying said seed or seeds; and grinding said seed or seeds to obtain a powder;

after said grinding, immersing said powder in a solvent to separate an oil component from said powder;

separating insoluble residue from said solvent to obtain defatted residue;

immersing said defatted residue in a second solvent;

extracting said rosemarinic acid from said defatted residue, to form a first solution; and separating the first solution comprising said second solvent and rosemarinic acid from said defatted residue, wherein said extracting further comprises:

heating said defatted residue immersed in said second solvent in a reflux condenser;

UNITED STATES PATENT AND TRADEMARK OFFICE
CERTIFICATE OF CORRECTION

PATENT NO. : 6,444,839 B1
DATED : September 3, 2002
INVENTOR(S) : Tateo Murui

It is certified that error appears in the above-identified patent and that said Letters Patent is hereby corrected as shown below:

wherein said separating step further comprises:

dissolving said first solution in water;

adding ethyl acetate to said first solution dissolved in water to form a mixture;

separating a second solution comprising ethyl acetate and said rosemarinic acid from said mixture;

dissolving said second solution in water to form a third solution;

removing insoluble material from said third solution;

separating a fourth solution comprising said rosemarinic acid from said third solution by column fractionation; and concentrating said fourth solution by vacuum concentration, wherein a rosemarinic acid content of said fourth solution after said vacuum concentration is 98.5 to 99.1 percent by weight.--

Signed and Sealed this

Twenty-eighth Day of October, 2003

JAMES E. ROGAN
*Director of the United States Patent and Trademark Office*